(12) United States Patent
Huang et al.

(10) Patent No.: US 6,782,732 B2
(45) Date of Patent: Aug. 31, 2004

(54) METHOD FOR NON-DESTRUCTIVE STRESS WAVE TESTING OF WOOD

(75) Inventors: Yan-San Huang, Shindian (TW); Shin-Shin Chen, Taipei (TW)

(73) Assignee: Taiwan Forestry Research Institute, Taipei (TW)

( * ) Notice: Subject to any disclaimer, the term of this patent is extended or adjusted under 35 U.S.C. 154(b) by 23 days.

(21) Appl. No.: 10/360,628

(22) Filed: Feb. 10, 2003

(65) Prior Publication Data

US 2004/0144158 A1 Jul. 29, 2004

(51) Int. Cl.[7] ................................................. G01N 3/30
(52) U.S. Cl. ........................ 73/12.07; 73/774; 73/597
(58) Field of Search ............................. 73/12.01, 12.07, 73/12.09, 760, 774, 597

(56) References Cited

U.S. PATENT DOCUMENTS

| | | | | |
|---|---|---|---|---|
| 4,722,223 A | * | 2/1988 | Bach et al. .................... 73/579 |
| 4,858,469 A | * | 8/1989 | Hosgood et al. .............. 73/579 |
| 5,060,516 A | * | 10/1991 | Lau et al. ...................... 73/602 |
| 5,396,799 A | * | 3/1995 | Ross et al. .................... 73/579 |
| 5,760,308 A | * | 6/1998 | Beall et al. .................... 73/644 |
| 6,347,542 B1 | * | 2/2002 | Larsson et al. ............. 73/12.09 |
| 6,598,477 B2 | * | 7/2003 | Floyd ........................... 73/597 |
| 6,715,337 B2 | * | 4/2004 | Huang et al. ............. 73/12.12 |
| 2003/0150277 A1 | * | 8/2003 | Andrews et al. .............. 73/801 |

* cited by examiner

*Primary Examiner*—Edward Lefkowitz
*Assistant Examiner*—T Miller
(74) *Attorney, Agent, or Firm*—Troxell Law Office PLLC

(57) ABSTRACT

The present invention discloses a method for evaluating the sound speed end dynamic modulus of elasticity of wood by non-destructive stress wave testing, wherein a timber specimen of long post is placed steadily on a sensor near the center with friction, acting on the interfaces of the sensor and the timber specimen, which resists the timber specimen from moving. Pounding one end of the timber specimen with a striking instrument sends a compression pulse stress wave down the post toward the other end, thereby generating a tension pulse wave back along the post till friction exponentially dissipates the energy of the stress waves. The changing signals of friction received by a receiver support the analyzer to measure longitudinal fundamental frequency of timber specimen; therefore, sound speed and dynamic modulus of elasticity are then calculated.

8 Claims, 3 Drawing Sheets

METHOD FOR NON-DESTRUCTIVE STRESS WAVE TESTING OF WOOD

FIELD OF THE INVENTION

The present invention relates to a method for non-destructive stress wave testing of wood and particularly to a method of calculating the sound speed and dynamic modulus of elasticity according to the longitudinal fundamental frequency of a timber specimen, which can be applied as a measurement on production line for enhancing conventional methods.

BACKGROUND OF THE INVENTION

Accordingly, destructive testing or non-destructive testing methods are usually adapted to estimate and measure the determinant factors of lumber qualities, such as moisture content, weight, wood grain, and modulus of elasticity. The foregoing non-destructive testing method is used to expertise the quality and the internal structure of lumber. For example, the wood strength is generally coinciding to the modulus of elasticity, whereby measuring the modulus of elasticity is wood strength estimated. The techniques for non-destructive testing of the modulus of elasticity include vibration, ultrasonic wave, and stress wave while these years method like Tap Tone is adapted to estimate the sound speed and dynamic modulus of elasticity by quickly measuring fundamental frequency with sound spectrum analysis. Tap Tone technique, as FIG. 3 shows, consists the follows steps. Sound receiver microphone 6, electrically connected to FFT spectrum analyzer 7, receives the sonic wave that is generated by the impact of hammer 9 on one end of timber specimen 8. FFT spectrum analyzer 7 will then measure the fundamental frequency with sound spectrum analysis, thereby calculating the sound speed and dynamic modulus of elasticity.

Only in quiet surroundings is Tap Tone technique an effective method for estimating the sound speed and dynamic modulus of elasticity of timber specimen 8; otherwise, the background noise causes microphone 6 to pick-up the feedback and causes FFT spectrum analyzer 7 to show inaccurate data. Except in a soundproof laboratory, Tap Tone method is unable to be adapted on general production line because microphone 6 may receive both the sonic wave of timber specimen 8 and the noises of the factory, thereby misleading the accuracy of the sound spectrum analysis. As a result, the conditions of background surroundings limit the usage of Top Tone technique.

SUMMARY OF THE INVENTION

It is, therefore, the main object of the present invention to calculate the sound speed and dynamic modulus of elasticity according to the longitudinal fundamental frequency of the timber specimen.

It is another object of the present invention to enable the present invention being used on production line for enhancing the conventional Tap Tone technique.

The foregoing object is accomplished by providing a method for non-destructive stress wave testing of wood, wherein a timber specimen is placed steadily on a sensor near the center with friction, acting on the interfaces of the sensor and the timber specimen, which resists said timber specimen from moving.

Pounding one end of said timber specimen with a striking instrument sends a compression pulse stress wave down the post toward the other end, thereby generating a tension pulse wave back along the post till friction exponentially dissipates the energy of the stress waves.

The changing signals of friction received by a receiver, electrically connected on said sensor, support an analyzer, electrically connected to said receiver, to measure longitudinal fundamental frequency of said timber specimen; therefore, sound speed and dynamic modulus of elasticity are then calculated.

BRIEF DESCRIPTION OF THE DRAWINGS

The present invention will be better understood from the following detailed description of preferred embodiments of the invention, taken in conjunction with the accompanying drawings, in which FIG. 1 Show a perspective diagram for non-destructive stress wave testing wood according to a preferred embodiment of the present invention.

DESCRIPTION OF THE PREFERRED EMBODIMENTS

Figure 1:
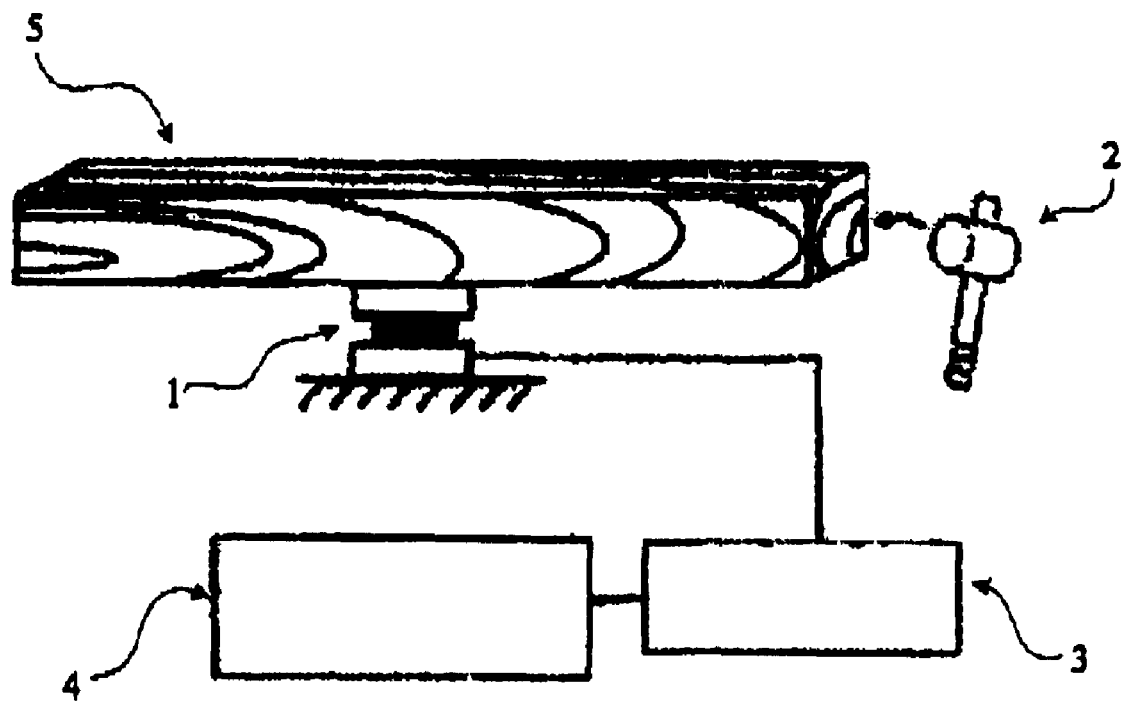
Figure 2:
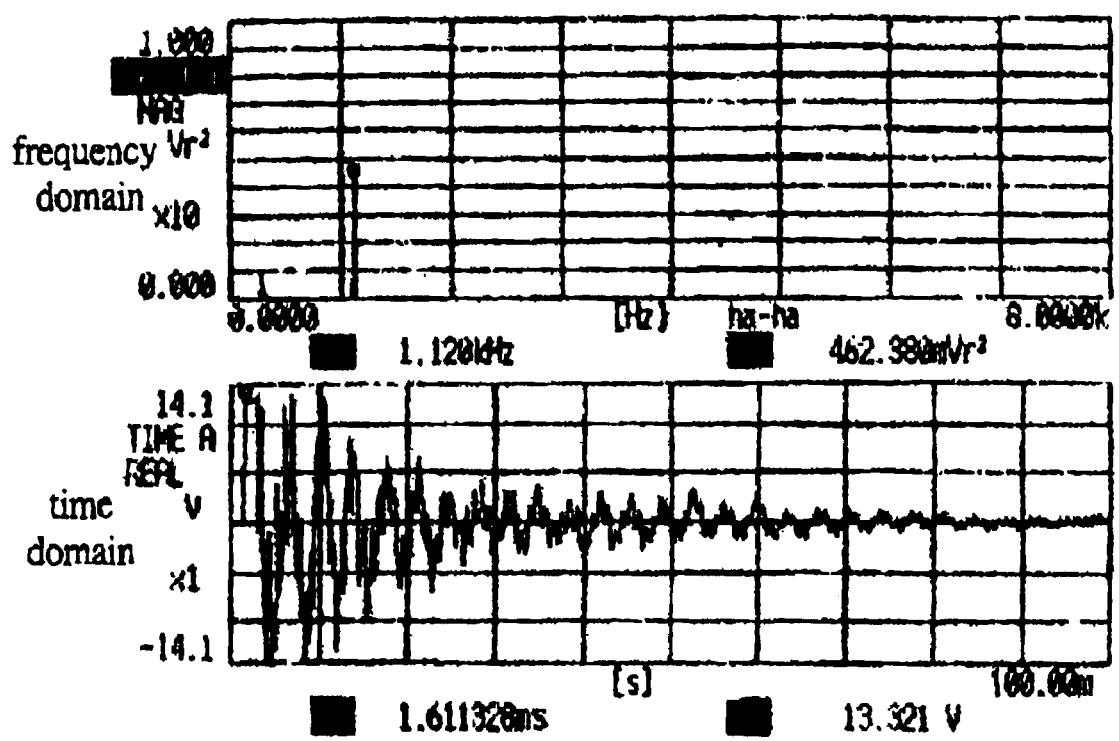
FIG. 2 show a response diagram for a stress waveform and fundamental frequency measured by the FFT spectrum analyzer of the present invention.
Figure 3:
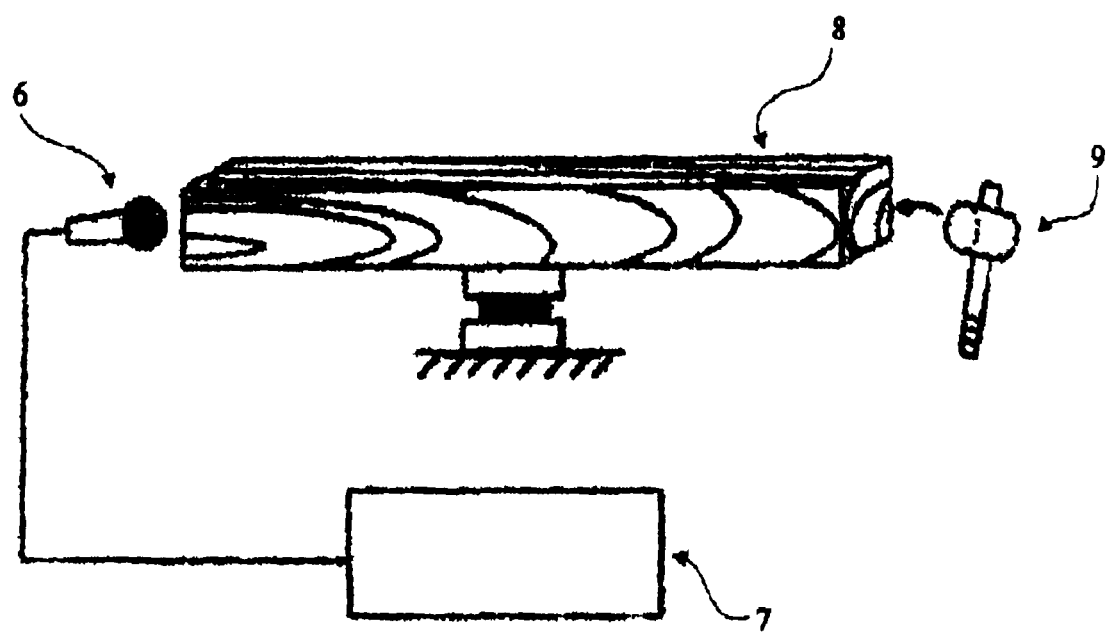
FIG. 3 show a perspective diagram of a conventional measurement.

FIG. 1 and FIG. 2 are reference for the preferred embodiment of the present invention and the stress waveform and fundamental frequency graphics measured by the analyzer of the present invention (FFT spectrum analyzer). As the pictures show, this invention discloses a method for non-destructive stress wave testing of wood, wherein timber specimen 5 is placed steadily near the center on sensor 1, which may be a 3-component dynamometer, with friction, acting on the interfaces of sensor 1 and timber specimen 5, which resists timber specimen 5 from moving.

Pounding one end of timber specimen 1 with striking instrument 2, which may be a hammer, sends a compression pulse stress wave down the post toward the other and of timber specimen 5, thereby generating a tension pulse wave back along the post till friction exponentially dissipates the energy of the stress waves.

The changing signals of friction received by receiver 3, which may be a charge amplifier, electrically connected on sensor 1, support analyzer 4, which may be FFT spectrum analyzer, electrically connected to receiver 3, to measure longitudinal fundamental frequency of timber specimen 5, shown on said FFT spectrum analyzer. (Referring to FIG. 2) The frequency of stress wave measured by the foregoing demonstration is exactly same as that measured by the conventional Tap Tone technique. That is, the present invention is able to offer a method for measuring fundamental frequency for the calculation of the sound speed and dynamic modulus of elasticity.

In order to calculate sound speed, fundamental frequency and the length of said timber specimen are used as basic numbers. The formula hereof is $v=2frL$, wherein $v$ is sound speed, $fr$ is fundamental frequency, and $L$ is the length of said timber specimen.

With the density of said timber specimen and the foregoing sound speed, the dynamic modulus of elasticity of said timber specimen can be calculated. The formula hereof is $Ed=v^2\rho$, wherein $Ed$ refers to dynamic modulus of elasticity, $v$ refers to sound speed, and $\rho$ refers to the density of said timber specimen. Consequently, the present invention can be adapted to calculate the sound speed and dynamic modulus of elasticity according to the longitudinal fundamental frequency of the timber specimen and can be applied as a measurement on production line for enhancing the conventional Tap Tone technique.

In the foregoing detailed description, it is understood that the previous objects of present invention can be achieved for those skilled in art, whereby the patent application will be issued according to patent application conditions.

The foregoing description is only used to illustrate the preferred embodiments of the present invention, not intended to limit the scope thereof. Variations and modifications exist within the scope and spirit of the invention as described and as defined in the following claims.

What is claimed is:

1. A method for non-destructive stress wave testing of wood comprising:

a timber specimen of long post placed on a sensor near the center with friction, acting on the interfaces of said sensor and said timber specimen, resisting said timber specimen from moving;

one end of said timber specimen pounded with striking instrument, sending a stress wave down the post toward the other end, thereby generating a tension pulse wave back along the post till friction exponentially dissipates the energy of said stress waves;

the changing signals of friction received by a receiver electrically connected on said sensor;

said signals analyzed with an analyzer electrically connected to said receiver, whereby fundamental frequency of said timber specimen is measured; and the sound speed and dynamic modulus of elasticity calculated according to said fundamental frequency.

2. The method for non-destructive stress wave testing of wood according to claim 1, wherein said sensor is a 3-component dynamometer.

3. The method for non-destructive stress wave testing of wood according to claim 1, wherein said striking instrument is a hammer.

4. The method for non-destructive stress wave testing of wood according to claim 1, wherein said receiver is a charge amplifier.

5. The method for non-destructive stress wave testing of wood according to claim 1 wherein said analyzer is a FFT spectrum analyzer.

6. The method for non-destructive stress wave testing of wood according to claim 1, wherein said sound speed is calculated according to the length of said timber specimen and said fundamental frequency; and said dynamic modulus of elasticity is calculated according to said sound speed and the density of said timber specimen.

7. The method for non-destructive stress wave testing of wood according to claim 6, wherein said sound speed calculate with equation of v=2frL where v is a sound speed, fr is a fundamental frequency; and L is a length of timber specimen.

8. The method for non-destructive stress wave testing of wood according to claim 6, wherein said dynamic modulus of elasticity calculate with equation of Ed=$v^2\rho$ where Ed is a dynamic modulus of elasticity, v is a sound speed; and $\rho$ is a density of timber specimen.

* * * * *